(12) United States Patent
Jacoby et al.

(10) Patent No.: US 10,441,386 B2
(45) Date of Patent: Oct. 15, 2019

(54) DENTAL IMPLANT

(75) Inventors: Yuval Jacoby, Tel-Aviv (IL); Nitzan Bichacho, Tel-Aviv (IL)

(73) Assignee: MIS Implants Technologies Ltd., Misgav (IL)

( * ) Notice: Subject to any disclaimer, the term of this patent is extended or adjusted under 35 U.S.C. 154(b) by 0 days.

(21) Appl. No.: 14/123,289

(22) PCT Filed: Jun. 3, 2012

(86) PCT No.: PCT/IL2012/000218
§ 371 (c)(1),
(2), (4) Date: Dec. 2, 2013

(87) PCT Pub. No.: WO2012/164560
PCT Pub. Date: Dec. 6, 2012

(65) Prior Publication Data
US 2014/0106305 A1    Apr. 17, 2014

Related U.S. Application Data

(60) Provisional application No. 61/492,382, filed on Jun. 2, 2011.

(51) Int. Cl.
*A61C 8/00*    (2006.01)
*A61C 8/02*    (2006.01)

(52) U.S. Cl.
CPC .......... *A61C 8/0075* (2013.01); *A61C 8/0006* (2013.01); *A61C 8/0018* (2013.01);
(Continued)

(58) Field of Classification Search
CPC ... A61C 8/0075; A61C 8/0006; A61C 8/0018; A61C 8/0022; A61C 8/0066; A61C 8/0068; A61C 8/0069; A61C 8/0077
(Continued)

(56) References Cited

U.S. PATENT DOCUMENTS 4,722,688 A * 2/1988 Lonca ........................... 433/173
5,336,225 A * 8/1994 Zang .................. A61B 17/8605
411/398

(Continued)

FOREIGN PATENT DOCUMENTS

CN    103153225    6/2013
DE    102008063397    7/2010
(Continued)

OTHER PUBLICATIONS

International Search Report and the Written Opinion dated Sep. 13, 2012 From the International Searching Authority Re. Application No. PCT/IL2012/000218.
(Continued)

*Primary Examiner* — Cris L. Rodriguez
*Assistant Examiner* — Hao D Mai (57) ABSTRACT

A dental implant including an implant body having a top surface, and at least one non-annular cutaway portion longitudinally extending downwardly from the top surface along one side of the body and outwardly to the periphery, and a method for making the implant. The implant body preferably includes a body portion and a head portion integrally formed with the body portion, the body portion has a periphery and the head portion has a non-circular periphery, and the periphery of the head portion is smaller than the periphery of the body portion.

33 Claims, 12 Drawing Sheets

(52) U.S. Cl.
 CPC .......... *A61C 8/0022* (2013.01); *A61C 8/0066* (2013.01); *A61C 8/0068* (2013.01); *A61C 8/0069* (2013.01); *A61C 8/0077* (2013.01)

(58) Field of Classification Search
 USPC ................................................ 433/172–176
 See application file for complete search history.

(56) References Cited

U.S. PATENT DOCUMENTS

| | | | | |
|---|---|---|---|---|
| 5,454,811 | A * | 10/1995 | Huebner | A61B 17/8645 606/305 |
| 5,785,525 | A * | 7/1998 | Weissman | A61C 8/0018 433/174 |
| 6,001,100 | A * | 12/1999 | Sherman | A61F 2/0811 606/232 |
| 6,039,568 | A | 3/2000 | Hinds | |
| 6,723,099 | B1 * | 4/2004 | Goshert | A61B 17/0642 606/329 |
| 6,953,463 | B2 * | 10/2005 | West, Jr. | A61F 2/0811 606/326 |
| 7,309,231 | B2 | 12/2007 | Engman | |
| D616,097 | S * | 5/2010 | Johnson | D24/156 |
| 8,197,255 | B2 * | 6/2012 | Fromovich | A61C 8/0022 433/174 |
| 9,820,831 | B2 * | 11/2017 | Cho | A61C 8/0024 |
| 2004/0170946 | A1 * | 9/2004 | Lyren | A61C 8/0012 433/173 |
| 2006/0003290 | A1 | 1/2006 | Niznick | |
| 2006/0223030 | A1 | 10/2006 | Dinkelacker | |
| 2006/0269890 | A1 | 11/2006 | Mundwiler et al. | |
| 2007/0072148 | A1 | 3/2007 | Memmolo et al. | |
| 2009/0023109 | A1 * | 1/2009 | Jinton | A61C 8/0025 433/174 |
| 2009/0092944 | A1 * | 4/2009 | Pirker | A61C 8/0036 433/173 |
| 2009/0239195 | A1 * | 9/2009 | Wohrle et al. | 433/174 |
| 2011/0070558 | A1 * | 3/2011 | Park | A61B 17/863 433/174 |
| 2012/0178049 | A1 | 7/2012 | Holmstrom et al. | |
| 2012/0264085 | A1 * | 10/2012 | Hansson | A61C 8/0022 433/174 |
| 2013/0230825 | A1 | 9/2013 | Kenk et al. | |
| 2013/0244203 | A1 | 9/2013 | Magnusson et al. | |
| 2014/0030674 | A1 | 1/2014 | Nguyen | |
| 2016/0317253 | A1 | 11/2016 | Duerr | |
| 2017/0049539 | A1 | 2/2017 | Jacoby et al. | |

FOREIGN PATENT DOCUMENTS

| | | |
|---|---|---|
| EP | 1882458 | 1/2008 |
| EP | 1943980 | 7/2008 |
| JP | 2013-078428 | 5/2013 |
| KR | 10-1050236 | 7/2011 |
| KR | 10-2013-0113776 | 10/2013 |
| WO | WO 97/06930 | 2/1997 |
| WO | WO 01/06944 | 2/2001 |
| WO | WO 2005/065571 | 7/2005 |
| WO | WO 2008/157137 | 12/2008 |
| WO | WO 2008/157138 | 12/2008 |
| WO | WO 2010/072211 | 7/2010 |
| WO | WO 2012/164560 | 12/2012 |
| WO | WO 2012/173577 | 12/2012 |
| WO | WO 2013/037729 | 3/2013 |
| WO | WO 2013/037730 | 3/2013 |
| WO | WO 2015/125139 | 8/2015 |

OTHER PUBLICATIONS

International Preliminary Report on Patentability dated Dec. 12, 2013 From the International Bureau of WIPO Re. Application No. PCT/IL2012/000218.

Notice of Reason fopr Rejection dated Mar. 25, 2016 From the Japanese Patent Office Re. Application No. 2014-513308 and Its Translation Into English.

International Preliminary Report on Patentability dated Sep. 1, 2016 From the International Bureau of WIPO Re. Application No. PCT/IL2015/050185.

Decision of Rejection dated Sep. 29, 2016 From the State Intellectual Property Office of the People's Republic of China Re. Application No. 201280037636.2 and Its Translation Into English.

Notification of Office Action and Search Report dated Nov. 2, 2015 From the State Intellectual Property Office of the People's Republic of China Re. Application No. 201280037636.2.

Translation Dated Nov. 17, 2015 of Notification of Office Action and Search Report dated Nov. 2, 2015 From the State Intellectual Property Office of the People's Republic of China Re. Application No. 201280037636.2.

Notification of Office Action and Search Report dated Jun. 20, 2016 From the State Intellectual Property Office of the People's Republic of China Re. Application No. 201280037636.2.

Translation of Notification of Office Action dated Jun. 20, 2016 From the State Intellectual Property Office of the People's Republic of China Re. Application No. 201280037636.2.

Request for Examination dated May 23, 2016 From the ROSPATENT, Federal Government Institutions, Federal Institute of Industrial Property of the Federal Service for Intellectual Property, Patent and Trademarks of the Russian Federation Re. Application No. 2013158082 and Its Translation Into English.

Communication Relating to the Results of the Partial International Search dated Jun. 23, 2015 From the International Searching Authority Re. Application No. PCT/IL2015/050185.

International Search Report and the Written Opinion dated Aug. 20, 2015 From the International Searching Authority Re. Application No. PCT/IL2015/050185.

Office Action dated Jan. 18, 2017 From the Israel Patent Office Re. Application No. 229758 and Its Translation Into English. (5 Pages).

Examination Report dated Nov. 9, 2016 From the Republica de Colombia, Superintendencia de Industria y Comercio Re. Application No. NC2016/0000996 and Its Translation Into English. (4 Pages).

Office Action dated Dec. 22, 2016 From the Israel Patent Office Re. Application No. 229758 and Its Translation Into English. (6 Pages).

Official Decision of Rejection dated Nov. 4, 2016 From the Japan Patent Office Re. Application No. 2014-513308 and Its Translation Into English. (9 Pages).

Examination Report dated Sep. 16, 2016 From the Republica de Colombia, Superintendencia de Industria y Comercio Re. Application No. NC2016/0000996 and Its Translation Into English.

Communication Pursuant to Article 94(3) EPC dated Sep. 18, 2017 From the European Patent Office Re. Application No. 12793774.6 (4 Pages).

Notification of Reexamination dated Jun. 28, 2017 From the State Intellectual Property Office of the People's Republic of China Re. Application No. 201280037636.2 and Its Translation Into English. (19 Pages).

Decision of Reexamination dated Jan. 24, 2018 From the State Intellectual Property Office of the People's Republic of China Re. Application No. 201280037636.2. (17 Pages).

Restriction Official Action dated Nov. 16, 2017 From the US Patent and Trademark Office Re. U.S. Appl. No. 15/119,775. (7 pages).

Decision of Reexamination dated Jan. 24, 2018 From the State Intellectual Property Office of the People's Republic of China Re. Application No. 201280037636.2 and Its Machine Translation Into English. (44 Pages).

Communication Pursuant to Article 94(3) EPC dated Sep. 12, 2018 From the European Patent Office Re. Application No. 15713237.4.

Restriction Official Action dated Aug. 28, 2018 U.S. Appl. No. 15/119,775. (9 pages).

Summons to Attend Oral Proceedings Pursuant to Rule 115(1) EPC Dated Jul. 19, 2018 From the European Patent Office Re. Application No. 12793774.6. (6 Pages).

(56) References Cited

OTHER PUBLICATIONS

Translation Dated Jun. 28, 2018 of Notification of Office Action dated May 31, 2018 From the State Intellectual Property Office of the People's Republic of China Re. Application No. 201580020795.5. (4 Pages).
Notification of Office Action and Search Report dated May 31, 2018 From the State Intellectual Property Office of the People's Republic of China Re. Application No. 201580020795.5 and Its Summary in English. (8 Pages).
Notice of Preliminary Rejection dated Feb. 18, 2019 From the Korean Intellectual Property Office, Patent Examination Policy Office Re. Application No. 10-2013-7035023 and Its Translation Into English. (11 Pages).
Provision of the Minutes in Accordance With Rule 124(4) EPC dated Apr. 10, 2019 From the European Patent Office Re. Application No. 12793774.6. (8 Pages).
Applicant-Initiated Interview Summary dated Dec. 4, 2018 From the US Patent and Trademark Office Re. U.S. Appl. No. 15/119,775. (3 Pages).
Applicant-Initiated Interview Summary dated Dec. 26, 2018 From the US Patent and Trademark Office Re. U.S. Appl. No. 15/119,775. (3 Pages).
Notice of Reason for Rejection dated Jan. 22, 2019 From the Japan Patent Office Re. Application No. 2016-553475 and Its Translation Into English. (9 Pages).
Notification of Office Action and Search Report dated Jan. 21, 2019 From the State Intellectual Property Office of the People's Republic of China Re. Application No. 201580020795.5. (9 Pages).
Translation Dated Feb. 14, 2019 of Notification of Office Action dated Jan. 21, 2019 From the State Intellectual Property Office of the People's Republic of China Re. Application No. 201580020795.5. (6 Pages).
Supplementary European Search Report and the European Search Opinion dated Nov. 4, 2014 From the European Patent Office Re. Application No. 12793774.6.
Abuhussein et al. "The Effect of Thread Pattern Upon Implant Osseointegration", Clinical Oral Implant Research, 21: 129-136, 2010.

* cited by examiner

PRIOR ART

DENTAL IMPLANT

FIELD OF THE INVENTION

The present invention relates to the field of dental implants and, more particularly, to the design of the implant's head that maximizes long term stability of the hard and soft tissues surrounding the implant, the abutment and the prosthesis connected to it.

BACKGROUND OF THE INVENTION

Dental implants are used to replace teeth that have been lost. An implant is placed in the jaw bone at the site of the missing tooth and a dental prosthetic unit is attached to it. The long term functional and aesthetic success of dental implants, and the prostheses attached to them, is determined by the response of the hard and soft tissues around them. Throughout the history of the art of dental implantology, it has been known that some bone loss and subsequent soft tissue recession always occur and have to be accepted.

Figure 1:
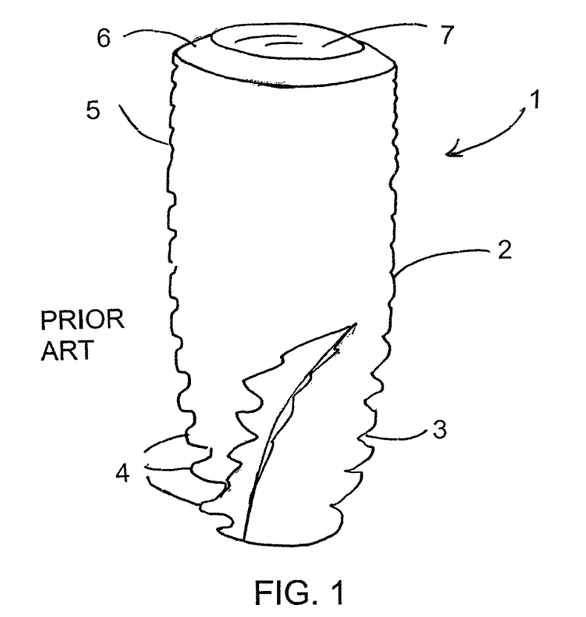
FIG. 1 is a schematic illustration of a prior art dental implant head.

In recent years, it has been shown that bone loss and soft tissue loss can be lessened by improving the tissue environment around the head of the implant and its connection with the prosthetic unit. Several implant designs having reduced connection diameter provided more soft tissue volume above the implant head and around the prosthetic abutment and have shown better hard and soft tissue responses. See, for example, the conventional, prior art implant 1 shown in FIG. 1 and shown, in use, in FIG. 2. Implant 1 includes a body 2 having a root-like apex 3, typically with screw threads 4 around the outside surface, and an implant head 5 having a top surface 6. A screw receiving bore 7 is defined in body 2 for receiving the prosthetic unit, typically an abutment having an abutment screw 8 and a crown 9 mounted on the abutment.

However, bone loss still occurs where there is less bone thickness around the implant head. This effect is most evident, and results in the most disturbing outcome, when it occurs in the thin bone plates buccal to implants placed in the anterior region of the mouth where the tissues are exposed in the smile, as well as between adjacent implants, particularly in the anterior region. Dental professionals go to great lengths to prevent this effect by trying to locate the implant head away from the buccal plate, thus attempting to allow more bone thickness buccal to the implant head. But bone ridge size and implant dimensions may hinder their success.

Similarly, when adjacent implants are required, it may be difficult to leave sufficient space between the implants to permit the required tissue volume.

It is an established clinical fact that thicker buccal bone and larger bone volume are associated with reduced bone loss and reduced soft tissue loss. For that reason, smaller diameter implants are sometimes used in the anterior region of the mouth but at the expense of sacrificing mechanical strength of the fixture and of the connection or sacrificing prosthetic flexibility (such as when using one piece implants).

Figure 2:
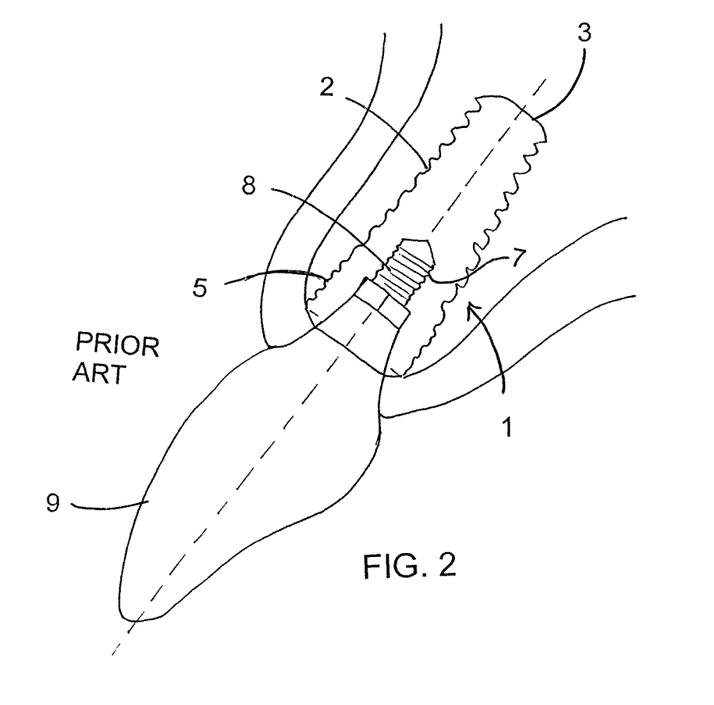

In addition, it is sometimes of great practical advantage to be able to directly access the abutment-to-implant connection screw through the crown unit. However, in the anterior maxillary regions, where it may be most desired to access from the lingual (palatal) direction, it is, in many cases, not possible due to the anatomy, size and orientation of the bone ridge (as seen in FIG. 2). To compensate for the angular limitations when restoring implants in the anterior maxillary region dentists sometimes resort to cemented crown solutions or use of angle-correcting prosthetic parts for screw retained crowns, which could sacrifice the preferred geometry of the sub-gingival prosthetic unit, the aesthetic outcome and connection strength (as by requiring smaller diameter screws).

Accordingly, there is a long felt need for a dental implant which results in reduced bone and soft tissue loss and which can be more successfully implanted in more problematic situations.

SUMMARY OF THE INVENTION

The present invention solves this problem by providing a modified head portion on the dental implant that allows more bone volume in critical locations around the implant head. At the same time, the mechanical strength of the implant and of the connection is maintained by retaining the remainder of the implant unchanged with reference to conventional implants. In this way, bone resorption and gum recession in critical areas around dental implants can be reduced.

There is thus provided, in accordance with the present invention, a dental implant including an implant body having a top surface, and at least one non-annular cutaway portion longitudinally extending downwardly from the top surface along one side of the body and outwardly to the periphery.

According to one embodiment of the invention, the dental implant further includes a screw receiving bore extending downwards from the top surface for coupling an abutment to the implant. The screw receiving bore may be concentric with the longitudinal axis of the implant, it may be non-concentric with the longitudinal axis of the implant, and/or it may be formed at an angle relative to the longitudinal axis of the implant.

According to another embodiment of the invention, the implant is a one-piece implant and the cut away portion extends along at least part of the intrabony portion and may include the trans-mucosal portion of the implant.

According to some embodiments, the cutaway portion is tapered. According to others, the cutaway portion ends in a shoulder. According to still others, the cutaway portion extends along the entire length of the body.

In some embodiments, there are two, oppositely disposed, cutaway portions longitudinally extending downwardly from the top surface along opposite sides of said body and outwardly to the periphery. In other embodiments, there are three cutaway portions longitudinally extending downwardly from the top surface, equidistant around the body and outwardly to the periphery.

Further according to the present invention, there is provided a dental implant including a body portion and a head portion integrally formed with the body portion, the head portion having a top surface; the body portion having a periphery and the head portion having a non-circular periphery; and wherein the periphery of the head portion is smaller than the periphery of the body portion.

There is further provided, in accordance with the invention, a method of forming a dental implant, the method including forming an implant body having a top surface; and cutting away at least one non-annular portion longitudinally extending downwardly from the top surface along one side of the body and outwardly to the periphery.

There is further provided, in accordance with the invention, a method of forming a dental implant, the method including providing a substantially cylindrical or conical implant body having a longitudinal axis; and forming a head portion having a top surface on the body. The head portion is formed by cutting away a portion of the periphery of the head portion so that the head portion has a non-circular periphery that is smaller than the periphery of the body.

BRIEF DESCRIPTION OF THE DRAWINGS

The present invention will be further understood and appreciated from the following detailed description taken in conjunction with the drawings in which:

FIG. 2 is a schematic sectional illustration of the prior art dental implant of

FIG. 1 in use;

DETAILED DESCRIPTION OF THE INVENTION

The present invention relates to a dental implant with a modified head portion that allows more bone in critical locations around the implant head without sacrificing the mechanical strength of the implant and of the connection. An object of the present invention is to reduce bone resorption in critical areas around dental implants by employing this modified design of the head of the implant.

Figure 3:
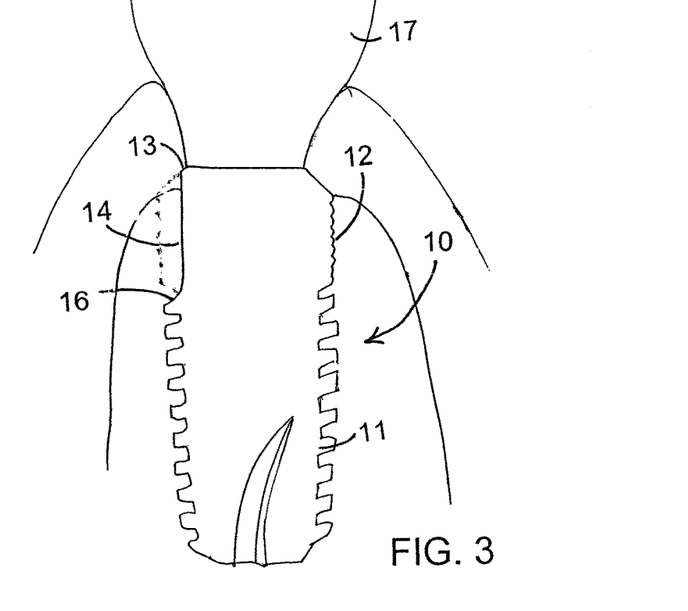
FIG. 3 is a schematic illustration of a dental implant constructed and operative in accordance with one embodiment of the present invention.
Figure 4:
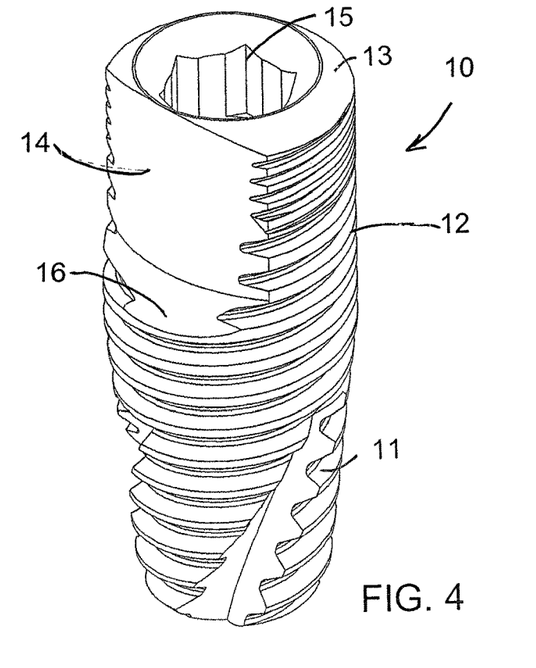
FIG. 4 is an isometric view of the implant head of the dental implant of FIG. 3.
Figure 5A:
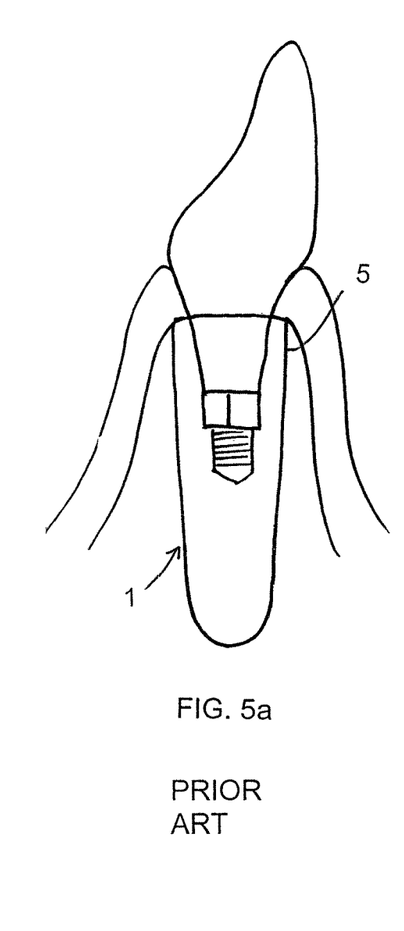
FIG. 5a is a schematic sectional view of a conventional prior art implant in use.
Figure 5B:
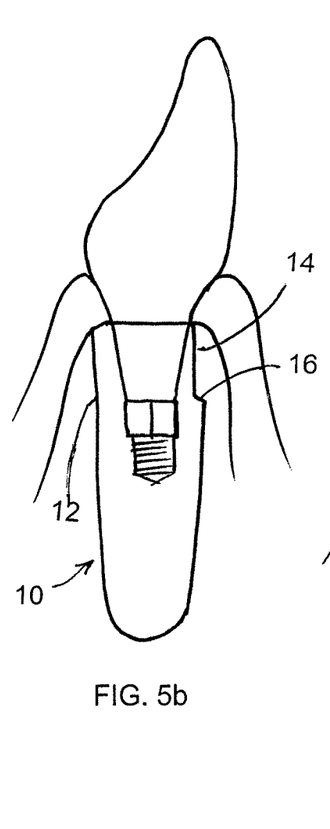
FIGS. 5b, 5c and 5d are schematic sectional views of implants according to different embodiments of the invention having flattened portions of different lengths.
Figure 5C:
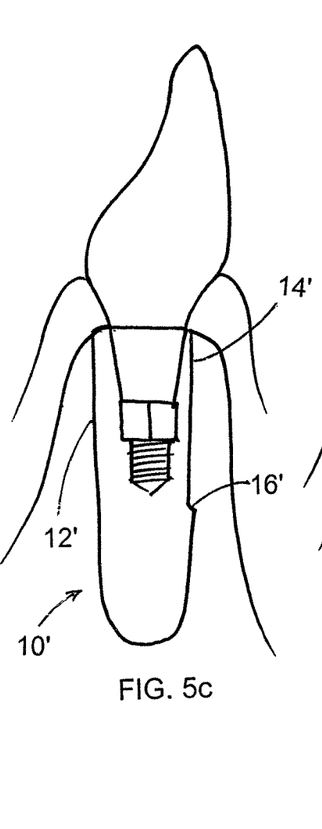
Figure 5D:
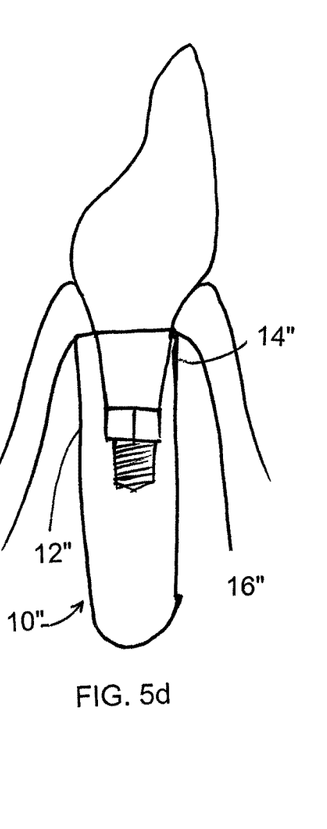

The new design involves providing an implant having a body and an integrally formed head of substantially smaller periphery than the periphery of the body, where the periphery of the head is not annular. The implant includes an implant body having a top surface from which one or more parts of the circumference of the predominantly tubular shape of the implant body are cut away from the top surface down to a desired height. The flattened surface allows more bone thickness adjacent to it, as compared to an implant having a full contour tubular shape, as the cutaway area becomes filled with new bone growth. The gain in bone thickness in critical areas, such as where there is a thin buccal bone plate or a thin mandibular ridge or between adjacent implants, is substantial and results in a lower risk of bone resorption and the consequent aesthetic compromise One example of an implant 10 according to the present invention is shown in cross-section in FIG. 3, and in an isometric view in FIG. 4. Implant 10 includes an implant body 11 and an implant head 12 defining a top portion 13. Head 12 has a longitudinal, non-annular cutaway portion 14, extending downwards from top portion 13 and outwards to the periphery of the implant. The result is that the head 12 has a smaller periphery than the body. Implant 10 also includes a screw receiving bore 15 for receiving an abutment screw (not shown) to hold a prosthetic unit 17. The cutaway portion 14 of the implant head 12 is indicated in broken lines in FIG. 3, to show the substantial difference in periphery of the head produced by the cut away portion 14. The cutaway portion can extend along the length of the implant as far as desired and may be parallel to the longitudinal axis of the implant or tapered at an angle to the longitudinal axis or may end in a shoulder 16, as in the embodiment Illustrated in FIG. 3. Several examples of flattened portions of different lengths are shown in FIGS. 5b, 5c and 5d, shown alongside a conventional prior art implant in FIG. 5a.

Figure 6A:
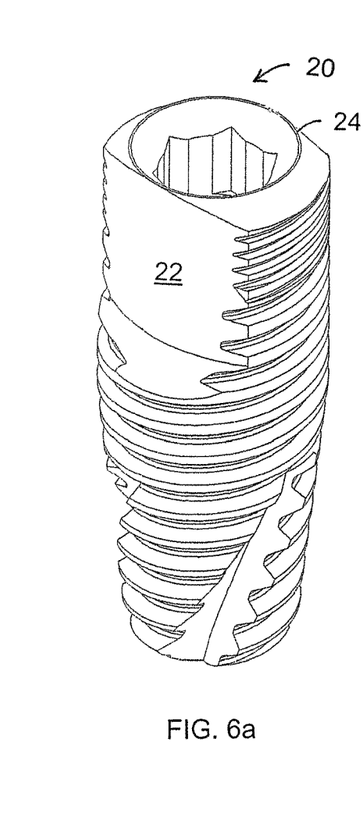
FIGS. 6a, 6b, 6c and 6d are isometric views of implants according to different embodiments of the invention having different arrangements of cutaway portions.
Figure 7A:
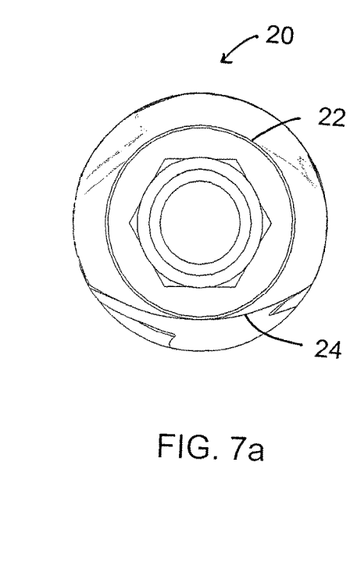
FIGS. 7a, 7b, 7c and 7d are top views of the implants of FIGS. 6a, 6b, 6c and 6d.
Figure 8A:
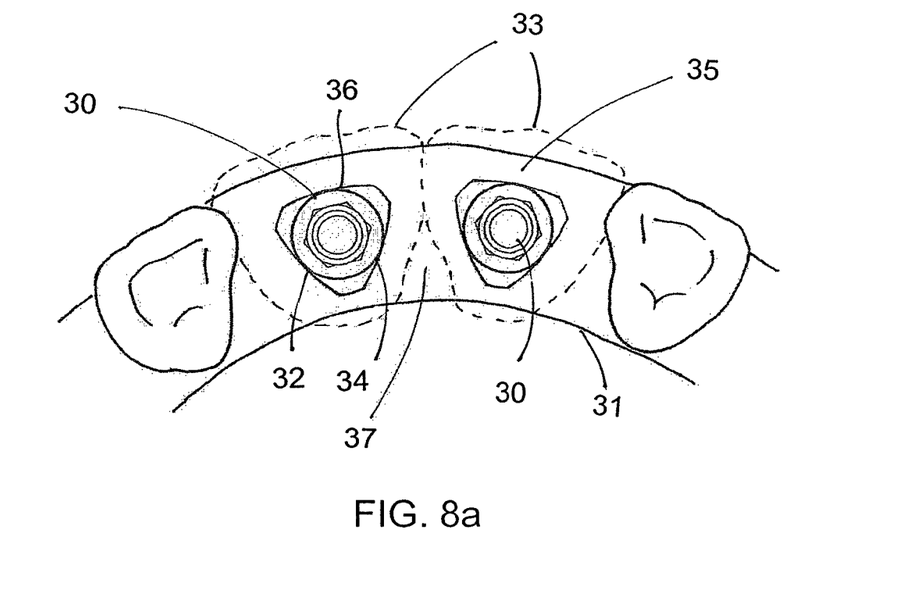
FIGS. 8a, 8b and 8c are schematic illustrations of three exemplary embodiments of implants according to the invention, in use.
Figure 8B:
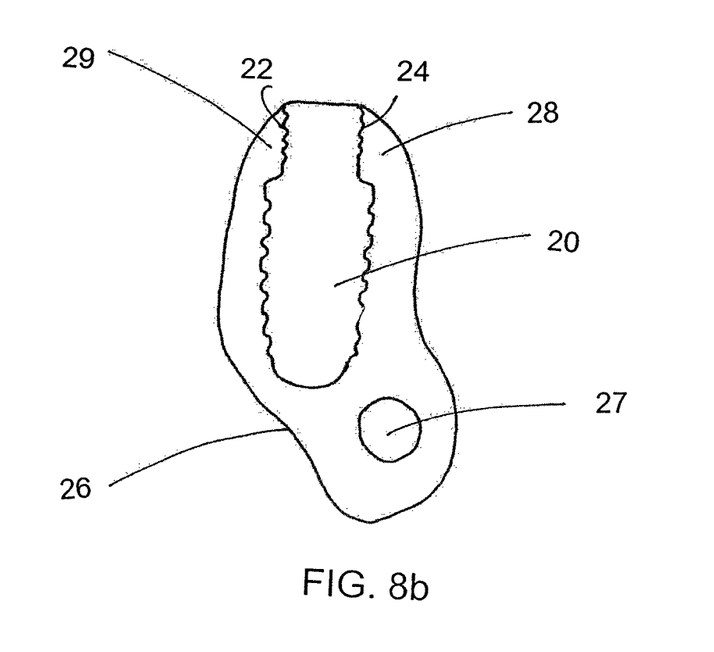

It should be noted that the topology of the cutaway portion of the implant head may be designed in any one of a variety of ways. The smaller periphery portion may be flat or planar, or it can be curved. If desired, the narrow periphery portion can have the same surface topology as the remainder of the head of the implant, for example, with microthreads or rings for improved adhesion to bone and tissue. As stated above, the smaller periphery head portion may extend to include any part of the implant's length up to its entire length. In addition, more than one longitudinal cutaway portion may be provided, preferably arranged symmetrically around the body. For example, FIG. 6a is an isometric view and FIG. 7a is a top view of an implant 20 having two cut away portions 22, 24, one opposite the other. This type of implant is particularly suitable where the bone ridge is narrow, for example, in the posterior mandible. See, for example, FIG. 8b, showing a cross-section of a posterior mandible 26 with a mandibular nerve canal 27. An implant 20 having cut away portions 22, 24 is implanted therein. As can be seen, the body of the implant remains of conventional size to retain the mechanical strength of the fixture and of the connection in the bone, but the head has a smaller periphery to provide narrow emergence in the buccal/lingual dimension, which permits minimum bone loss around the implant head and enhanced soft tissue response. Thus, an enlarged area 28 of bone buccal to the implant head and an enlarged area 29 of bone lingual to the implant head relative to conventional implants are obtained.

Figure 6B:
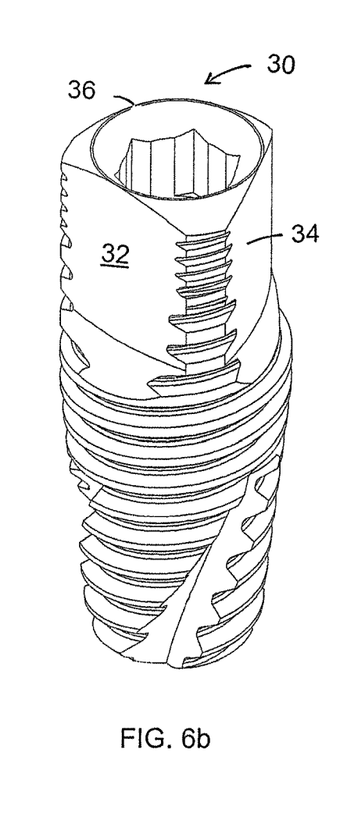
Figure 7B:
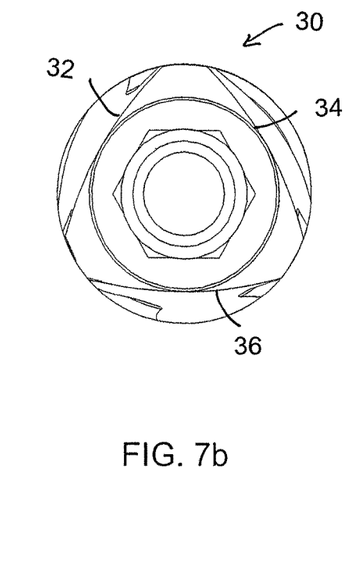

FIG. 6b shows an isometric view and FIG. 7b shows a top view of an implant 30 having three cutouts 32, 34, 36 equidistant about the longitudinal axis of the implant. This type of implant is particularly suitable for use with adjacent implants, particularly in areas where there is low bond volume buccal to the implant heads and between the implants. This design is particularly advantageous in the anterior part of upper jaw. See, for example, FIG. 8a, showing an occlusal view of an anterior maxillary bone crest 31 wherein two adjacent teeth 33 have been replaced with implants, after healing of the bone. Two implants 30 having cut away portions 32, 34, 36 are implanted in place of the two removed teeth. As can be seen, an enlarged area 35 of bone buccal to the implant heads and an enlarged area 37 of bone between the implant heads is provided, relative to conventional cylindrical (not cut away) implants.

Figure 6C:
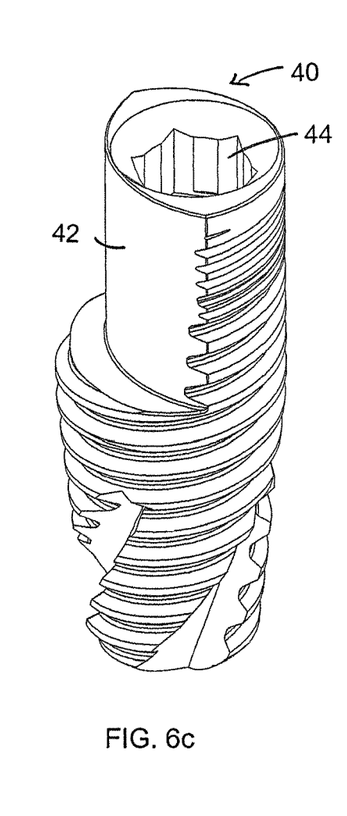
Figure 7C:
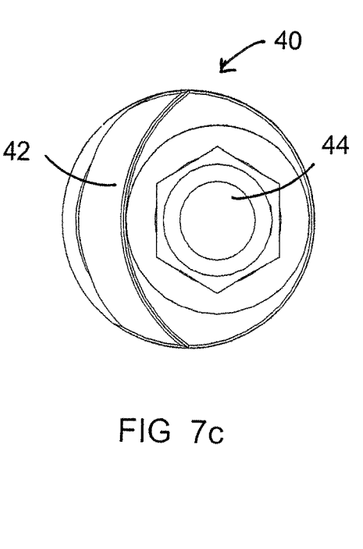

According to certain embodiments of the invention, the screw receiving bore for connecting the abutment is not concentric with the longitudinal axis of the implant. This permits the periphery of the implant head to be even smaller than in the symmetrical implant according to the invention described above. FIG. 6c shows an isometric view and FIG. 7c shows a top view of an implant 40 having a single cutout 42, similar to the implant of FIG. 4, but having an eccentrically disposed screw receiving bore 44 substantially aligned with the longitudinal axis of the implant. This design provides an implant having an even larger cutout area than the concentric implant of FIG. 4, particularly useful in areas where it is desired to provide extra (maximum) bone volume.

Figure 6D:
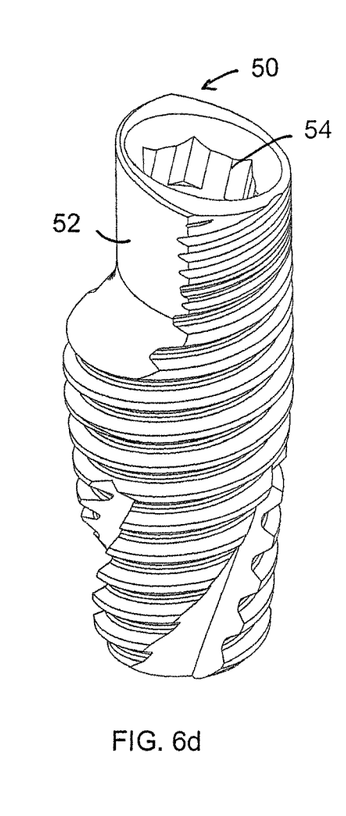
Figure 7D:
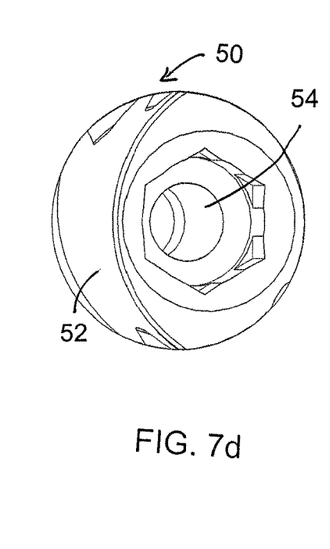
Figure 8C:
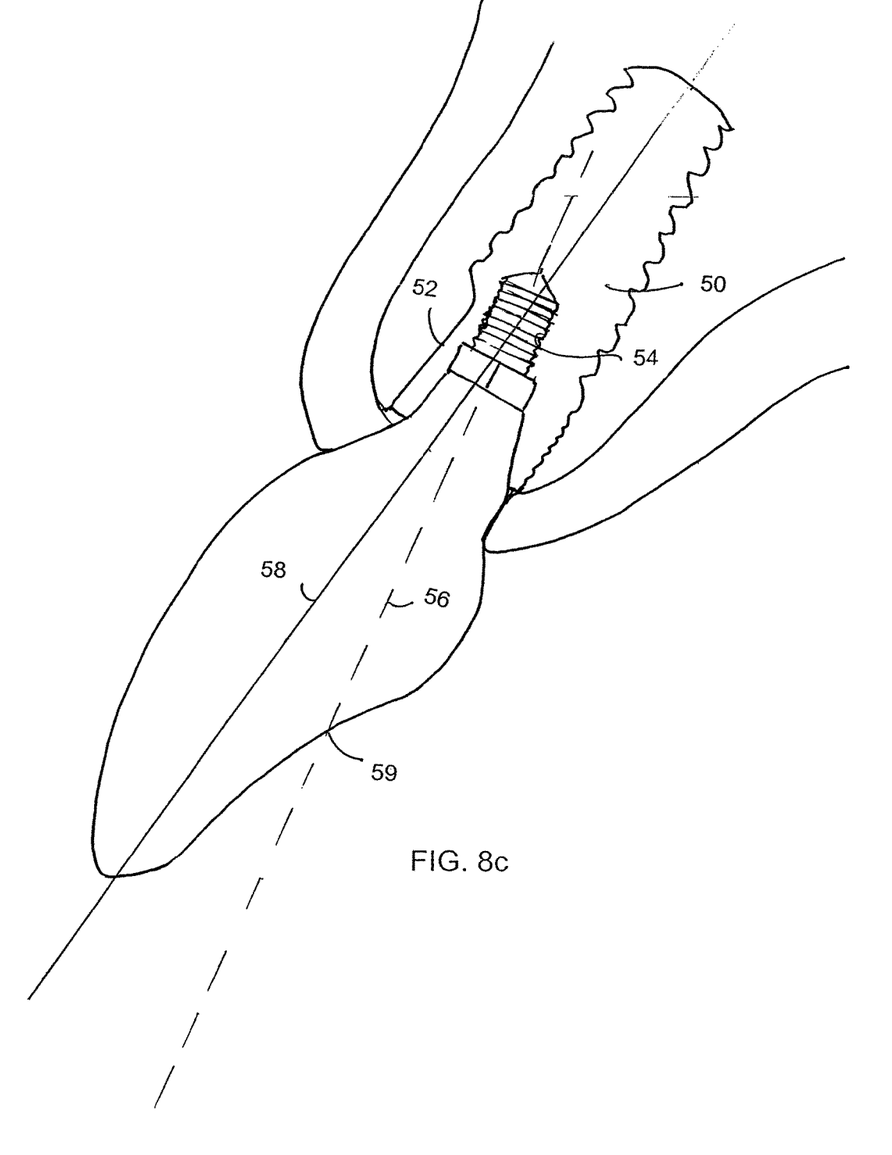

FIG. 6d shows an isometric view and FIG. 7d shows a top view of an implant 50 having a single cutout 52, similar to the implant of FIG. 6c, having a screw receiving bore 54 non-concentrically disposed relative to the longitudinal axis of the implant. However, in FIG. 6d, the screw receiving bore 54 is not aligned with the longitudinal axis of the implant but rather is formed at an angle thereto, as best seen in FIG. 7d. This design is particularly useful in the anterior region of the upper jaw to ensure extra volume of buccal bone and lingual access to the abutment screw. See, for example, FIG. 8c, where an implant 50 is shown, which has a screw receiving bore 54 having an axis 56 disposed at an angle to the longitudinal axis 58 of implant 50. It will be appreciated that this particular positioning allows for non symmetry in the location and angulation of the abutment connection and its screw relative to the implant. Thus, the connection and screw hole centers can be positioned more lingually (away from the cutout 52) and they can be oriented so as to greatly increase the probability that the abutment screw could be accessed from the lingual aspect 59 of the restoration.

Figure 9A:
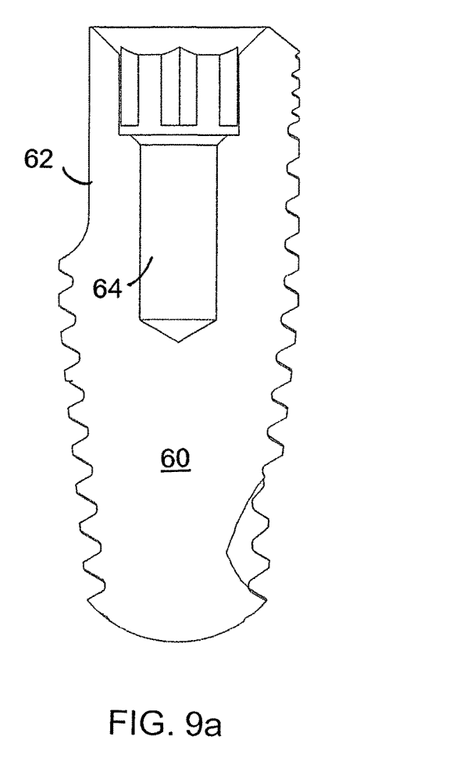
FIGS. 9a to 9d are side sectional illustrations of implants according to different exemplary embodiments of the invention.
Figure 9B:
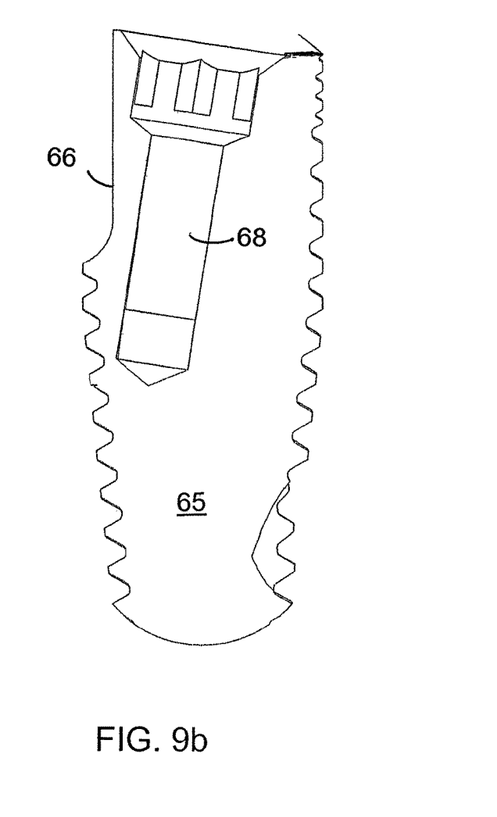
Figure 9C:
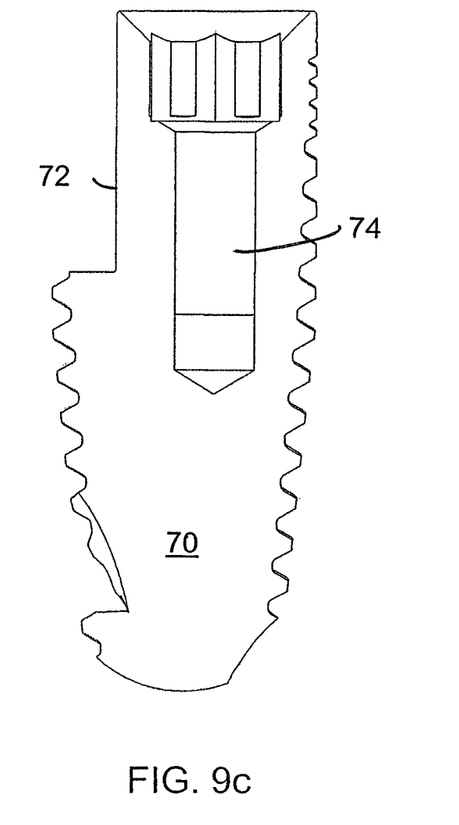
Figure 9D:
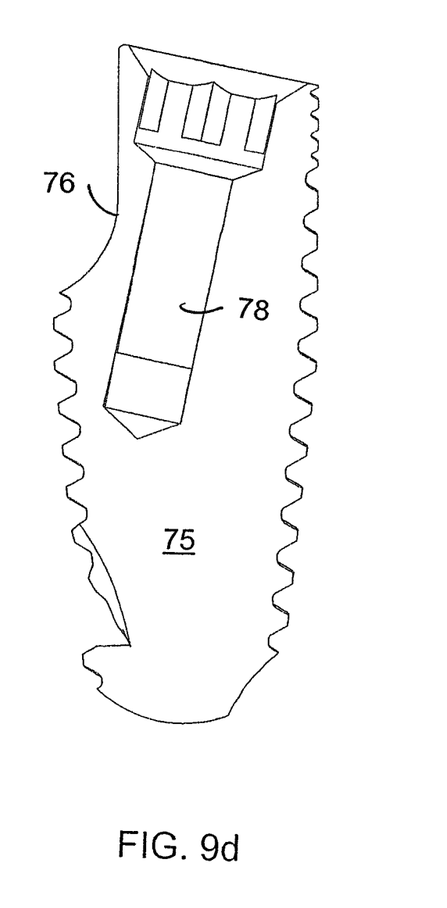

The connection itself (the interface between implant and abutment) could be tilted and in line with the tilted screw or, alternatively, the connection could be kept parallel to the longitudinal axis of the implant with just the screw hole and screw access tilted toward the lingual. FIGS. 9a, 9b, 9c and 9d provide side sectional illustrations of the various angular possibilities. FIG. 9a shows an implant 60 with a cutaway 62 and a screw receiving bore 64 concentrically located and aligned with respect to the longitudinal axis of the implant. FIG. 9b shows an implant 65 with a cutaway 66 and a screw receiving bore 68 concentrically located but tilted at an angle with respect to the longitudinal axis of the implant. FIG. 9c shows an implant 70 with a cutaway 72 and a screw receiving bore 74 eccentrically located but aligned with respect to the longitudinal axis of the implant. Thus, the cut away portion 72 is enlarged in width, relative to the implant of FIG. 9a. And FIG. 9d shows an implant 75 with a cutaway 76 and a screw receiving bore 78 eccentrically located and tilted at an angle with respect to the longitudinal axis of the implant. Thus, the cut away portion 76 can be enlarged in width, relative to the implant of FIG. 9b. It will be appreciated that any of these screw-receiving bore options can be used with any of the designs of implants described above and below and with any of the types of implants desired.

Thus, it will be appreciated that the particular design of the implant can be selected according to the location in the patient's mouth and the state of the patient's jaw.

Figure 10A:
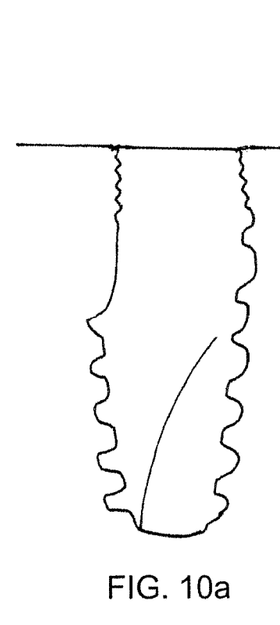
FIGS. 10a to 10e are side sectional views of implants of varying size and design, all formed according to different embodiments of the present invention.
Figure 10B:
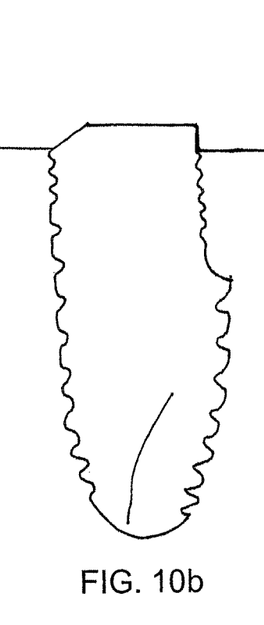
Figure 10C:
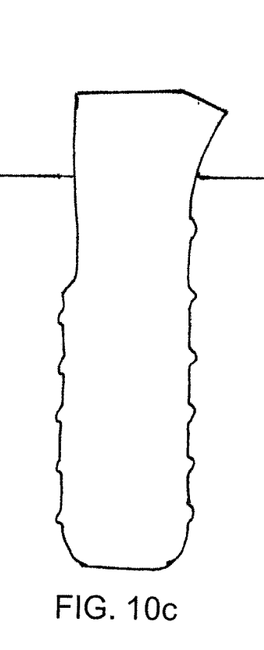
Figure 10D:
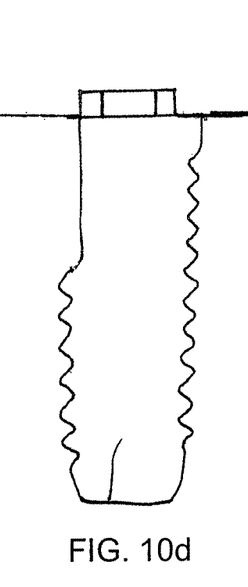
Figure 10E:
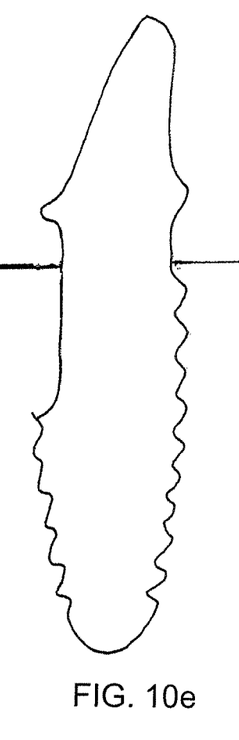

It will be appreciated that the modified head design disclosed in the present invention can be applied to all implant designs, regardless of body shape, thread type, length, diameter, connection, surface treatment and material used, or whether it is a bone level, tissue level or one-piece implant. See, for example, FIGS. 10a-10e, each illustrating a different type or design of implant implementing the cutaway portion of the present invention. FIG. 10a and FIG. 10b illustrate bone level implants. 10c illustrates a tissue level implant. FIG. 10d illustrates a bone level implant with an external connection and FIG. 10e illustrates a one-piece implant, having a prosthetic integrally formed with the implant body.

An implant with a single flattened or cut away area will have a single most proper (optimal) orientation (i.e., with the cut away area oriented adjacent the thin bone portion of the jaw). This type of implant, with a single cut away portion has a single proper orientation within a full 360 degree of rotational insertion and is better suited for smaller step, tighter thread implants or non-threaded implants. However, this characteristic may be a detriment in the case of threaded implants with a large thread step. While that may not be a problem in the anterior region where sub-bone-level positioning is often carried out, when this is an issue, the heads of the implants could be made with two or three cutouts, as illustrated above, so as to provide two-way or three-way symmetry. In this way, the implant can be rotated until any one of several cutout portions is disposed facing the problematic area of the jaw, so that additional bone growth will be possible in that area. These embodiments of the invention allow for smaller depth variability. A two cutout implant head allows two proper positions within every full rotation and a three cutout implant head allows three proper positions within every full rotation.

Similarly, proper, advantageous use of an implant incorporating the new design with the non concentric implant head (with just one cutout portion) requires a particular positioning of the implant head so that the cutout is always directed toward the area with reduced bone volume. Many times that would be towards the buccal. It will be appreciated that this particular positioning allows for non symmetry in the location and angulation of the abutment connection and its screw relative to the implant, as described above.

Figure 11A:
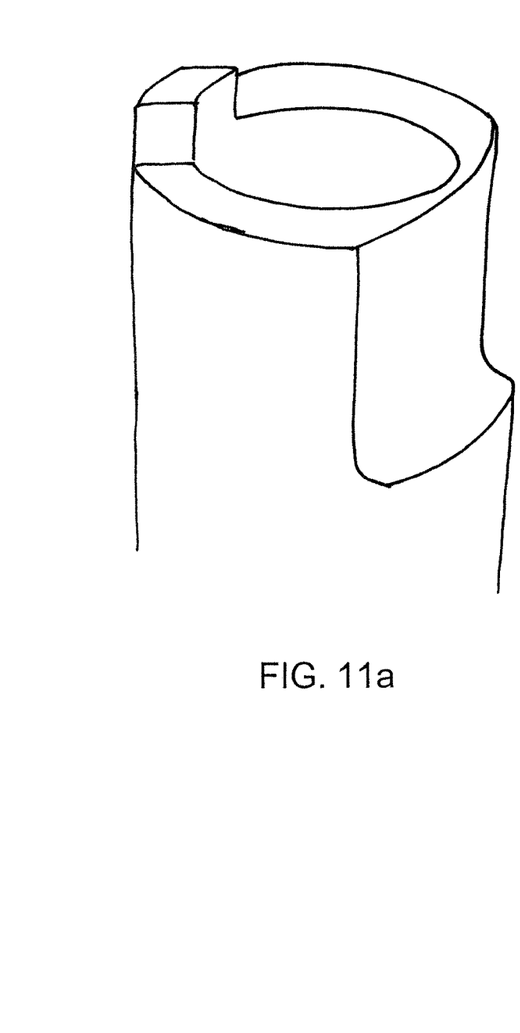
FIGS. 11a to 11c are schematic illustrations of implant heads according to further embodiments of the invention.
Figure 11B:
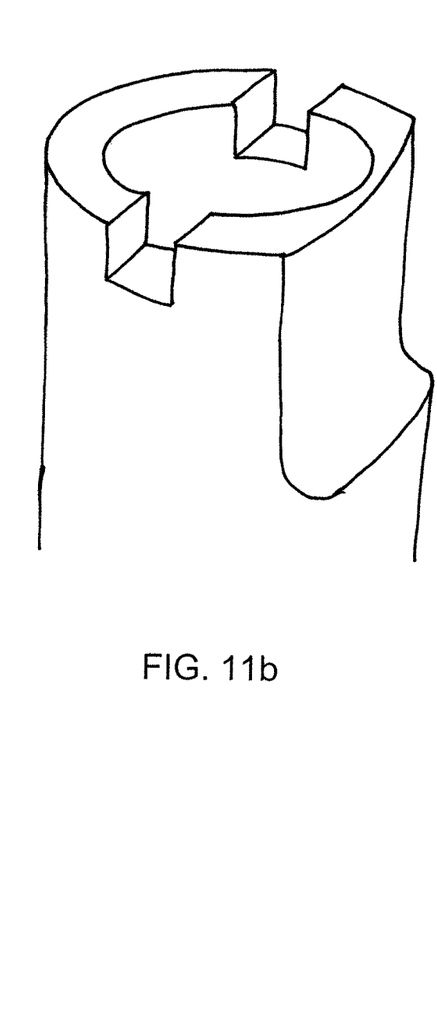
Figure 11C:
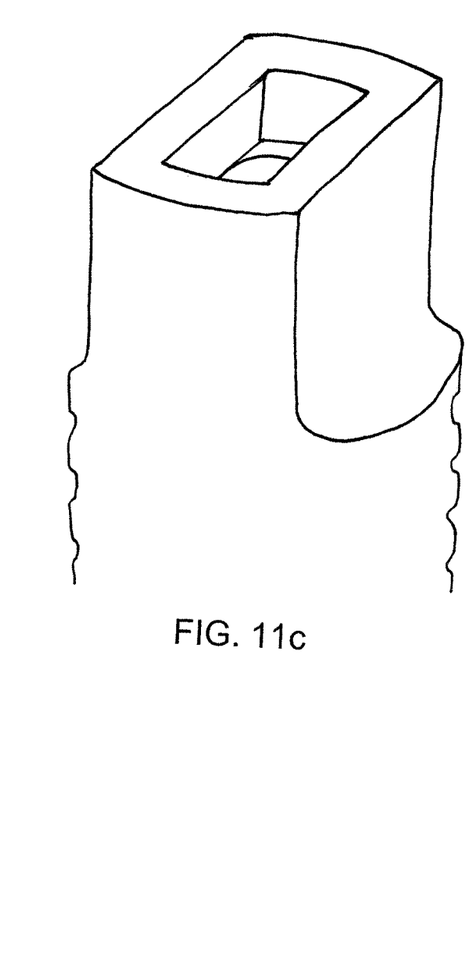

It should be noted that since the non concentric implant and the screw access are directionally confined, it is no longer necessary to adhere to rotational symmetry in the connection. Instead, the connection and the top surface of the implant could be made to suit the particular needs of such implant-abutment pair better than the conventional types of implant-abutment connections. Three exemplary instances of such a connection, having different features for receiving complementary features on the abutment, are depicted in FIGS. 11a, 11b and 11c. In FIG. 11a, the head defines a protrusion, in FIG. 11b, the head defines a flattened portion with notches, and in FIG. 11c, the head defines a rectangular connection.

Figure 12A:
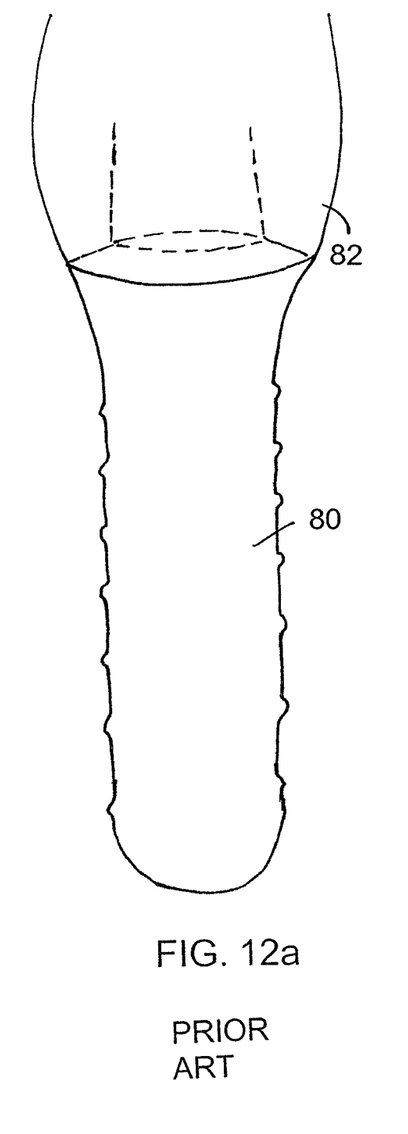
FIG. 12a is a schematic of a conventional prior art implant head with prosthetic unit.
Figure 12B:
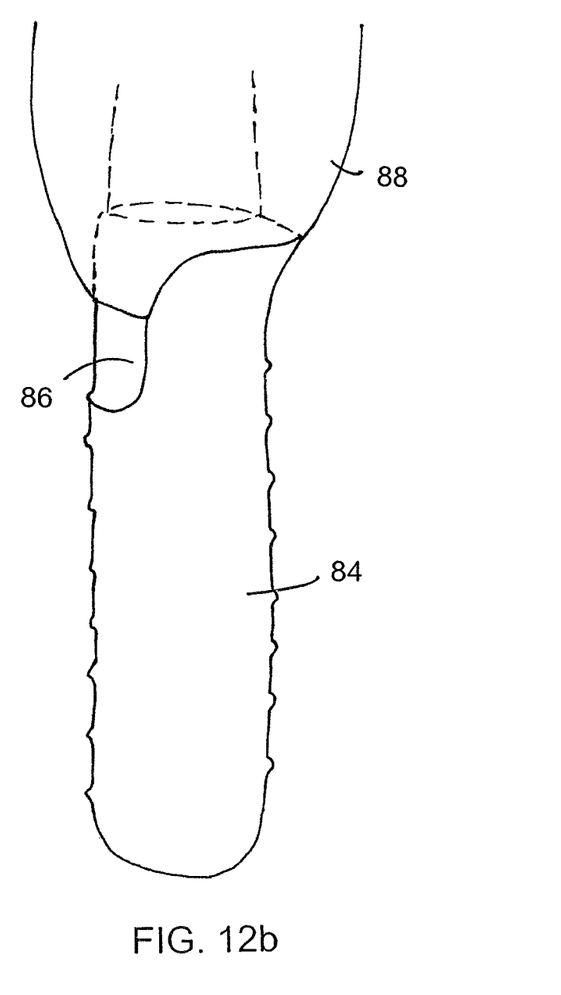
FIG. 12b is a schematic illustration of a dental implant according to a further embodiment of the invention. It will be appreciated that the drawings are only schematic and are not to scale.

A further advantage of the implants of the present invention is illustrated schematically in FIGS. 12a, showing a prior art implant 80 with a prosthetic unit 82, and an implant 84, illustrated in FIG. 12b, according to one embodiment of the present invention. Implant 84 has a single cutaway 86 as described above. Prior art implant 80 is a tissue level implant where bone and tissue loss may occur. When it does, the metal implant 80 becomes visible. That may be very disturbing, particularly if located in the anterior portion of the mouth. The implant 84 of the present invention permits the prosthetic crown 88 to be extended along part or all of the length of the cut away portion 86. This portion is disposed to be visible in the mouth, so that even if there is some bone or tissue loss, the metal implant 84 will not be visible.

It will be appreciated that the above descriptions are intended only to serve as examples and that many other embodiments are possible and encompassed within the spirit and the scope of the present invention. The implants described herein and illustrated in the figures are examples only. Implants embodying other variations of the structures described here are within the scope of the present invention.

While the invention has been described with respect to a limited number of embodiments, it will be appreciated that many variations, modifications and other applications of the invention may be made. It will further be appreciated that the invention is not limited to what has been described hereinabove merely by way of example. Rather, the invention is limited solely by the claims which follow.

The invention claimed is:

1. A dental implant for implantation in a jaw bone, comprising:
    an implant body having a screw thread along an outer threaded region, wherein the implant body is sized for threaded rotation into bone for positioning of an intrabony portion of the outer threaded region within said jaw bone;
    said intrabony portion having a top, proximally facing surface of a proximal end of the implant body from which three cutaway surfaces extend downwardly towards an apical portion on a distal end of the implant body and extend outwards to a periphery of said implant body, said surfaces at overlapping axial position with said thread, a longitudinal axis of said body defined between said intrabony portion and said apical portion;
    wherein said three cutaway surfaces are arranged around the periphery of the implant body and spaced apart circumferentially, and each of said cutaway surfaces defines an outside cutaway volume, each of said volumes being positionable by rotation guided by said threaded region to face a portion of said jaw bone, to create a volume below bone level for filling with new bone growth;
    wherein said cutaway surfaces are flat or convex in a direction along said periphery; and
    wherein at least one of said three cutaway surfaces ends in a shoulder extending radially outward to the periphery of said implant body; and wherein said shoulder is located between said proximal and said distal end.

2. The dental implant according to claim 1, further comprising:
    a screw-receiving bore extending downwards from the top surface for coupling an abutment to the implant.

3. The dental implant according to claim 2, wherein said bore is eccentrically disposed from the longitudinal axis of the body.

4. The dental implant according to claim 3, wherein:
    at least one said three cutaway surfaces extends to a point not radially further from the longitudinal axis of said body than a radius of said eccentrically disposed bore.

5. The dental implant according to claim 2, wherein said screw-receiving bore is formed at an angle to the longitudinal axis of the body.

6. The dental implant according to claim 2, wherein:
    at least one of said three cutaway surfaces is at least as wide as a diameter of said screw-receiving bore.

7. The dental implant of claim 2, wherein at least one of said three cutaway surfaces extends longitudinally at least from said bone level to at least a threaded region of said screw-receiving bore.

8. The dental implant of claim 2, wherein at least one of said three cutaway surfaces extends longitudinally at least from said bone level beyond said screw-receiving bore.

9. The dental implant of claim 1, comprising a head region having microthreads or rings around a periphery thereof, and at least one of said three cutaway surfaces extends longitudinally at least from said bone level to beyond said microthreads or rings.

10. The dental implant according to claim 1, wherein at least one of said three cutaway surfaces is substantially parallel to said longitudinal axis.

11. The dental implant according to claim 1, wherein at least one of said three cutaway surfaces extends along said body to said apical portion.

12. The dental implant according to claim 1 wherein said three cutaway surfaces longitudinally extend from the top surface of said body, wherein said three cutaway surfaces are disposed equidistantly around the body.

13. The dental implant according to claim 1, wherein:
    said intrabony portion includes a body portion on the distal end of said implant body and a head portion on the proximal end of the implant body, said head portion integrally formed with said body portion;
    said head portion having a non- circular periphery;
    said body portion and said head portion having lengths such that a portion of said head portion is positioned below bone level in said jaw bone when said implant is implanted in a jaw bone bore sized to receive it; and
    wherein said non-circular periphery of said head portion is smaller than a periphery of the body portion.

14. The dental implant according to claim 1, wherein:
    said intrabony portion includes a body portion on the distal end of said implant body and a head portion on the proximal end of the implant body, said head portion integrally formed with said body portion;
    said body portion and said head portion are longitudinally sized such that a portion of said head portion is positioned below bone level in said jaw bone when said implant is implanted in a jaw bone bore sized to receive it; and
    said portion of said head portion comprises a portion of said three cutaway surfaces.

15. The dental implant according to claim 1, wherein:
    said three cutaway surfaces are flat extending along a width of said implant.

16. The dental implant of claim 1, wherein at least one of said three cutaway surfaces extends along and is oriented at a tapering angle to said longitudinal axis of the implant body.

17. The dental implant of claim 1, wherein said three cutaway surfaces are convex along said periphery.

18. The dental implant of claim 1, wherein said three cutaway surfaces extend to the top surface of said implant such that said top surface has a non-circular face with a perimeter defined by said cutaway surfaces.

19. A method of encouraging bone growth in a jaw bone near a dental implant, comprising:
    selecting a dental implant having a longitudinal axis and having an intrabony portion having an outer screw thread, wherein said intrabony portion comprises three outer cutaway volumes spaced apart circumferentially at overlapping axial positions and arranged around a circumference of an implant body, wherein each of the three outer cutaway volumes extends from an intrabony portion top, proximally facing surface to at least a bone level of the dental implant while interrupting said outer screw thread and extends outwards to the circumference of said implant body, and wherein at least one of said three cutaway surfaces ends in a shoulder extending radially outward to the periphery of said implant body; and wherein said shoulder is located between said proximal and said distal end; and screwing the dental implant into a bore in said jaw bone, and axially positioning said dental implant while maintaining by rotation at least one of said three outer cutaway volumes adjacent to a thin portion of bone, by rotating in increments of a third of said circumference of said dental implant, wherein said thin portion comprises a portion of at least one from among the group consisting of a buccal plate and a mandibular ridge.

20. The method of claim 19, wherein said thin portion of bone comprises a critical area prone to bone resorption.

21. The method of claim 19, wherein:
said screwing comprises orienting, during said screwing, the three outer cutaway volumes relative to the jaw bone such that said volumes are adapted to fill with bone thickness gained by said thin portion of bone; and
said method further includes allowing new bone growth from said thin portion of bone into said volumes.

22. The method of claim 21, wherein said implant comprises a screw-receiving bore, and said orienting the volumes comprises positioning a center of said screw-receiving bore lingually relative to said bore in said jaw bone.

23. The method of claim 21, wherein said new bone growth is from the buccal plate.

24. The method of claim 21, wherein said new bone growth is from the mandibular ridge.

25. The method of claim 21, wherein said new bone growth is from a portion of bone adjacent to another bone implant.

26. The method of claim 19, wherein said dental implant comprises a screw-receiving bore, and at least one of said three outer cutaway volumes extends longitudinally at least from said bone level to at least a threaded region of said screw-receiving bore.

27. The method of claim 19, wherein said dental implant comprises a screw-receiving bore, and at least one of said three outer cutaway volumes extends longitudinally at least from said bone level beyond said screw-receiving bore.

28. The method of claim 19, wherein said dental implant comprises a head region having microthreads or rings around a periphery thereof, and at least one of said three outer cutaway volumes extends longitudinally at least from said bone level to beyond said microthreads or rings.

29. The method of claim 19, wherein said three outer cutaway volumes are equidistant around the implant body such that at least one of said three volumes flares towards said thin portion of bone.

30. The method of claim 19, wherein said positioning comprises maintaining a joining surface between two of said three outer cutaway volumes to face said thin portion of bone.

31. The method of claim 19, wherein said positioning comprises maintaining a joining surface between two of said three outer cutaway volumes to face the thin portion of bone and maintaining two of said volumes to face along a bony ridge and one of said volumes to face buccally or lingually.

32. The method of claim 19, wherein said positioning comprises positioning a convex portion of the implant to face said thin portion of bone.

33. A dental implant for implantation in a jaw bone, comprising:
an implant body having a screw thread along an outer threaded region, wherein the implant body is sized for threaded rotation into bone for positioning of an intrabony portion of the outer threaded region within said jaw bone;
said intrabony portion having a top, proximally facing surface of the implant body from which three cutaway surfaces extend downwardly towards an apical portion on a distal side of the implant body and extend outwards to a periphery of said implant body, said surfaces at overlapping axial position with said thread, a longitudinal axis of said body defined between said intrabony portion and said apical portion;
wherein said three cutaway surfaces are arranged around a circumference of the implant body and spaced apart circumferentially, and each of said cutaway surfaces defines an outside cutaway volume, each of said volumes being positionable by rotation guided by said threaded region to face a portion of said jaw bone, to create a volume below bone level for filling with new bone growth; and
wherein at least one of said three cutaway surfaces ends in a shoulder extending radially outward to the periphery of said implant body; and wherein said shoulder is located between said proximal and said distal end.

* * * * *